US010183447B2

(12) United States Patent
Chengalvarayan et al.

(10) Patent No.: US 10,183,447 B2
(45) Date of Patent: Jan. 22, 2019

(54) APPARATUS FOR CONNECTION OF THERMOPLASTIC TUBING

(71) Applicant: GE Healthcare Bio-Sciences AB, Uppsala (SE)

(72) Inventors: Kishore Chengalvarayan, Bangalore (IN); Manoj Ramakrishna, Bangalore (IN)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 336 days.

(21) Appl. No.: 15/030,560

(22) PCT Filed: Oct. 22, 2014

(86) PCT No.: PCT/SE2014/051240
§ 371 (c)(1),
(2) Date: Apr. 19, 2016

(87) PCT Pub. No.: WO2015/060774
PCT Pub. Date: Apr. 30, 2015

(65) Prior Publication Data
US 2016/0250806 A1     Sep. 1, 2016

(30) Foreign Application Priority Data

Oct. 24, 2013  (IN) ............... 3155/DEL/2013

(51) Int. Cl.
*A61M 39/14*       (2006.01)
*A61M 39/18*       (2006.01)
(Continued)

(52) U.S. Cl.
CPC ......... *B29C 65/7802* (2013.01); *A61M 39/14* (2013.01); *A61M 39/146* (2013.01);
(Continued)

(58) Field of Classification Search
CPC .... A61M 39/14; A61M 39/146; A61M 39/18; B29C 65/20; B29C 65/2046;
(Continued)

(56) References Cited

U.S. PATENT DOCUMENTS

| 4,369,779 A | 1/1983 | Spencer |
| 4,516,971 A | 5/1985 | Spencer |

(Continued)

FOREIGN PATENT DOCUMENTS

| CH | 698798 B1 | 10/2009 |
| CN | 1893991 A | 1/2007 |

(Continued)

OTHER PUBLICATIONS

Extended European Search Report Received for European Patent Application No. 14855384.5, dated Mar. 28, 2017, 9 pages.

(Continued)

*Primary Examiner* — Michael A Tolin
(74) *Attorney, Agent, or Firm* — Wood IP LLC

(57) ABSTRACT

The invention discloses an apparatus for aligning and supporting a first and a second length of thermoplastic tubing, preparatory to and during cutting and welding of said lengths of tubing, that includes a first holder arranged to accommodate portions of the first and second lengths of tubing in a first and a second elongated holding space respectively, a second holder arranged to accommodate portions of the first and second lengths of tubing in a third and a fourth elongated holding space respectively, and movable in a direction essentially perpendicular to the holding spaces of the first and second holders from a cutting position, a cutting means arranged between said first and second holders for cutting said lengths of tubing when the second holder is in the cutting position and an aligning means to align these lengths of tubing with each other.

20 Claims, 8 Drawing Sheets

(51) Int. Cl.
  *B29C 65/20* (2006.01)
  *B29C 65/74* (2006.01)
  *B29C 65/78* (2006.01)
  *B29C 65/00* (2006.01)
  *B29K 27/06* (2006.01)
  *B29C 65/10* (2006.01)
  *B29C 65/14* (2006.01)
  *B29C 65/16* (2006.01)
  *B29L 31/00* (2006.01)
  *B29L 23/00* (2006.01)

(52) U.S. Cl.
  CPC ......... *A61M 39/18* (2013.01); *B29C 65/2046* (2013.01); *B29C 65/74* (2013.01); *B29C 65/7841* (2013.01); *B29C 66/1142* (2013.01); *B29C 66/5221* (2013.01); *B29C 66/73921* (2013.01); *B29C 66/8414* (2013.01); *B29C 66/857* (2013.01); *B29C 65/103* (2013.01); *B29C 65/1412* (2013.01); *B29C 65/16* (2013.01); *B29C 66/71* (2013.01); *B29K 2027/06* (2013.01); *B29L 2023/007* (2013.01); *B29L 2031/753* (2013.01)

(58) Field of Classification Search
  CPC ... B29C 65/74; B29C 65/743; B29C 65/7802; B29C 65/7841; B29C 66/1142; B29C 66/5221; B29C 66/73921; B29C 66/8414; B29C 66/857; B29K 2027/06; B29L 2023/007
  See application file for complete search history.

(56) References Cited

U.S. PATENT DOCUMENTS

| | | | |
|---|---|---|---|
| 4,521,263 A | 6/1985 | Benin et al. | |
| 5,248,359 A * | 9/1993 | Shaposka | A61M 39/146 156/158 |
| 7,371,305 B2 | 5/2008 | Sano et al. | |
| 7,657,996 B2 | 2/2010 | Sano et al. | |
| 2003/0141009 A1 | 7/2003 | Landherr et al. | |
| 2006/0180526 A1 | 8/2006 | Sugawara et al. | |
| 2007/0149914 A1 | 6/2007 | Axelsson | |

FOREIGN PATENT DOCUMENTS

| | | | | |
|---|---|---|---|---|
| EP | 0515811 A2 | 12/1992 | | |
| EP | 3060292 A1 | 8/2016 | | |
| JP | 59-025756 A | 2/1984 | | |
| JP | 59-071814 A | 4/1984 | | |
| JP | 06-091010 A | 4/1994 | | |
| JP | H0820070 A | 1/1996 | | |
| JP | 09-206383 A | 8/1997 | | |
| JP | H09206383 B2 | 8/1997 | | |
| JP | 2004089315 A | 3/2004 | | |
| JP | 2004187737 A | 7/2004 | | |
| JP | 2010082222 A | * | 4/2010 | ......... B29C 65/2046 |
| JP | 2010082222 A | | 4/2010 | |
| WO | 2015/060774 A1 | 4/2015 | | |

OTHER PUBLICATIONS

International Search Report and Written Opinion regarding International Application No. PCT/SE2014/051240, dated Feb. 11, 2015, 15 pages.

Chinese Office Action and Search Report Received for Chinese Patent Application 201480058189.8 dated Aug. 24, 2018, 20 pages (11 pages Official Copy + 9 Pages English Translation).

Japan Notice of Preliminary Rejection for Japanese Patent Application No. 2016-524460, dated Sep. 4, 2018, 6 pages.

* cited by examiner

APPARATUS FOR CONNECTION OF THERMOPLASTIC TUBING

CROSS-REFERENCE TO RELATED APPLICATIONS

This application is a filing under 35 U.S.C. 371 of international application number PCT/SE2014/051240, filed Oct. 22, 2014, which claims priority to Indian application number IN 3155/DEL/2013, filed Oct. 24, 2013, the entire disclosures of each of which are hereby incorporated by reference.

TECHNICAL FIELD OF THE INVENTION

The present invention relates to sterile connection of thermoplastic tubing, and more particularly to an apparatus for sterile connection by welding. The invention also relates to a method of sterile connection of thermoplastic tubing by welding.

BACKGROUND OF THE INVENTION

The biotechnology industry uses different manufacturing systems for creating aseptic and sterile connections between process containers and equipment, such as plastic bags and pumps. A known manufacturing system uses controlled environments such as clean rooms or cabinets to ensure aseptic connections during manufacture. When necessary connections are made in such a controlled environment that breaches sterile tubing and piping, the environment does not contaminate the fluid flow passage. However, maintaining a clean room is time consuming, difficult and costly to validate For example separation or reaction systems such as chromatography systems, filter systems or bioreactor systems have today at least partly been provided as disposable systems. This eliminates the need for cleaning and cleaning validation before processing, in between processes and cycles or after processing before re-use as required for conventional re-usable equipment. With disposable systems cross-contamination is avoided.

Bioburden control of single-use equipment during manufacturing of the equipment itself is required to eliminate cleaning needs before bringing single-use equipment into product contact. This is usually achieved by manufacturing of single-use equipment in controlled environment (clean room), often followed by sterilisation processes (gamma irradiation). The demands of the level of bioburden control can differ for different applications. However, bioburden control to a certain degree of the equipment is not only required for some applications, but also considered as the preferable for most of the applications using disposable equipment. The production of this equipment in controlled environments is required to guarantee a low initial level of contaminants prior to the bioburden control procedure. Sterility and asepsis are terms used to define the state of a system, a piece of equipment or a fluid conduit as being in control of bioburden levels to different degrees.

Many manufacturing systems use disposable plastic bags connected to flexible thermoplastic tubes, which requires special connections to assure that the bags and tubes remain clean and sterile. Known are also pre-sterile bags and tube sets which can be supplied with the appropriate special disposable aseptic connection system fittings already in place. These connections are simple, repeatable and validatable but they normally have to be applied during manufacture of the sets and are not amenable to the setting up of tailor-made systems directly in the bioprocess facility.

Sterile welding of flexible thermoplastic tubing, where lengths of tubing are cut and welded together under aseptic conditions is an attractive alternative which provides a higher degree of flexibility. Equipment for such welding is commercially available and different constructions have been described in e.g. U.S. Pat. No. 4,516,971, EP723851A2, WO2013096038A1, U.S. Pat. Nos. 7,398,813 and 6,705,372. Sterile welding is particularly common in medical settings, e.g. assembly of sterile circuits for hemodialysis. It is also quite commonly used in bioprocess settings, although a drawback of the available technology is that several separate welders have to be used for tubing of different diameters which are often used simultaneously in different parts of a single bioprocess to accommodate ranges of flow-rates, pressures etc.

Accordingly there is a need for a welding apparatus which enables welding of tubing over a range of different diameters.

SUMMARY OF THE INVENTION

One aspect of the invention is to provide a welding apparatus that enables aseptic welding of thermoplastic tubing having a range of different diameters. This is achieved with an apparatus as defined in claim 1.

One advantage is that the lengths of tubing to be joined by welding can be properly aligned irrespective of the tubing diameters. Further advantages are that straight and leak-free joints of high strength can be obtained.

Another aspect of the invention is to provide a method of welding thermoplastic tubing which allows aseptic welding independently of the tubing diameter over a range of diameters. This is achieved with a method as defined in the claims.

A third aspect of the invention is to provide a welding apparatus that enables aseptic welding of thermoplastic tubing having a range of different diameters. This is achieved with an apparatus as defined in the claims. One advantage of this apparatus is that the tubing holders can accommodate and align tubing of different diameters.

A fourth aspect of the invention is to provide a welding apparatus that enables aseptic welding of thermoplastic tubing having a range of different diameters. This is achieved with an apparatus as defined in the claims. One advantage of this apparatus is that tubing of different diameters can be securely clamped without over-compression of the tubing.

Further suitable embodiments of the invention are described in the dependent claims.

DETAILED DESCRIPTION OF EMBODIMENTS

Figure 1:
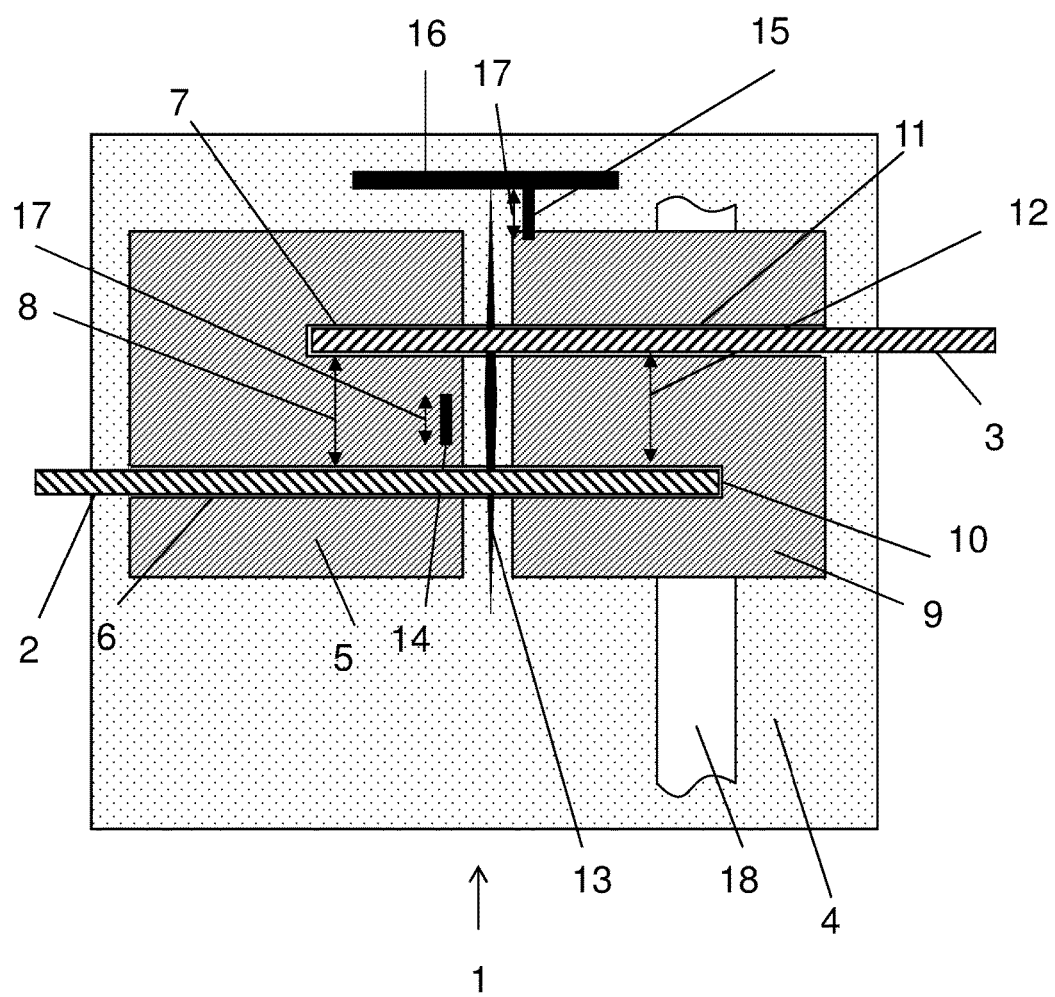
FIG. 1 shows an apparatus of the invention (top view), with the holders in the cutting position.
Figure 2:
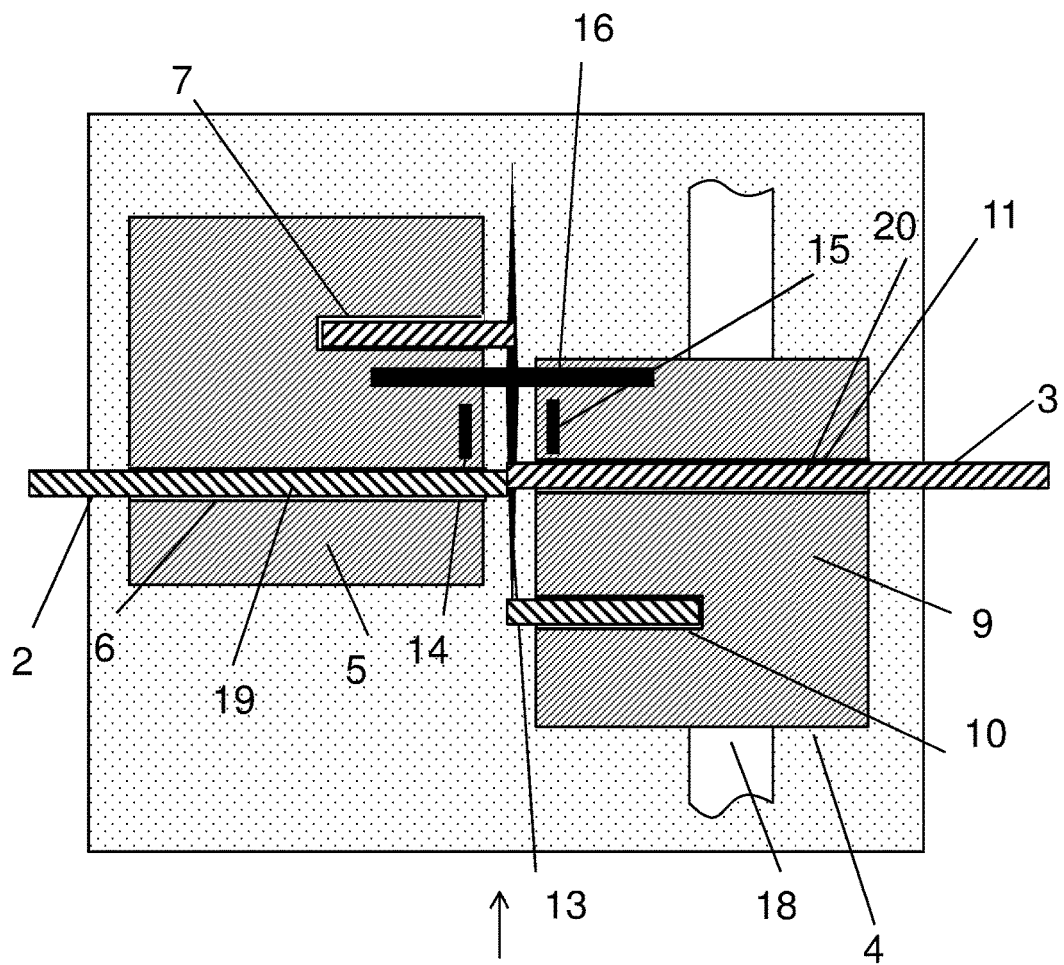
FIG. 2 shows the apparatus of FIG. 1 with the holders almost in the welding position, with incomplete alignment of the tubing lengths to be welded.
Figure 3:
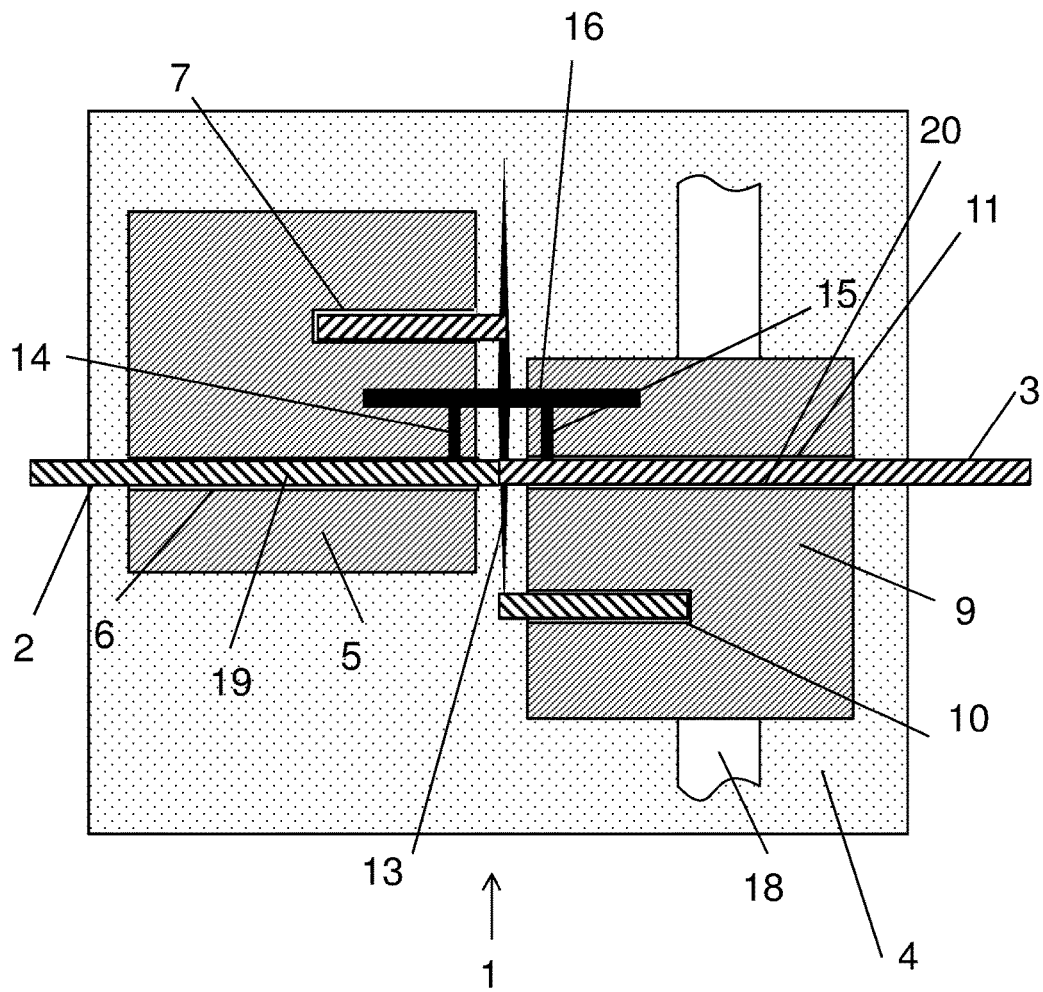
FIG. 3 shows the apparatus of FIG. 1 with the holders in the welding position, with the tubing lengths aligned by the aligning and abutment plates.
Figure 4:
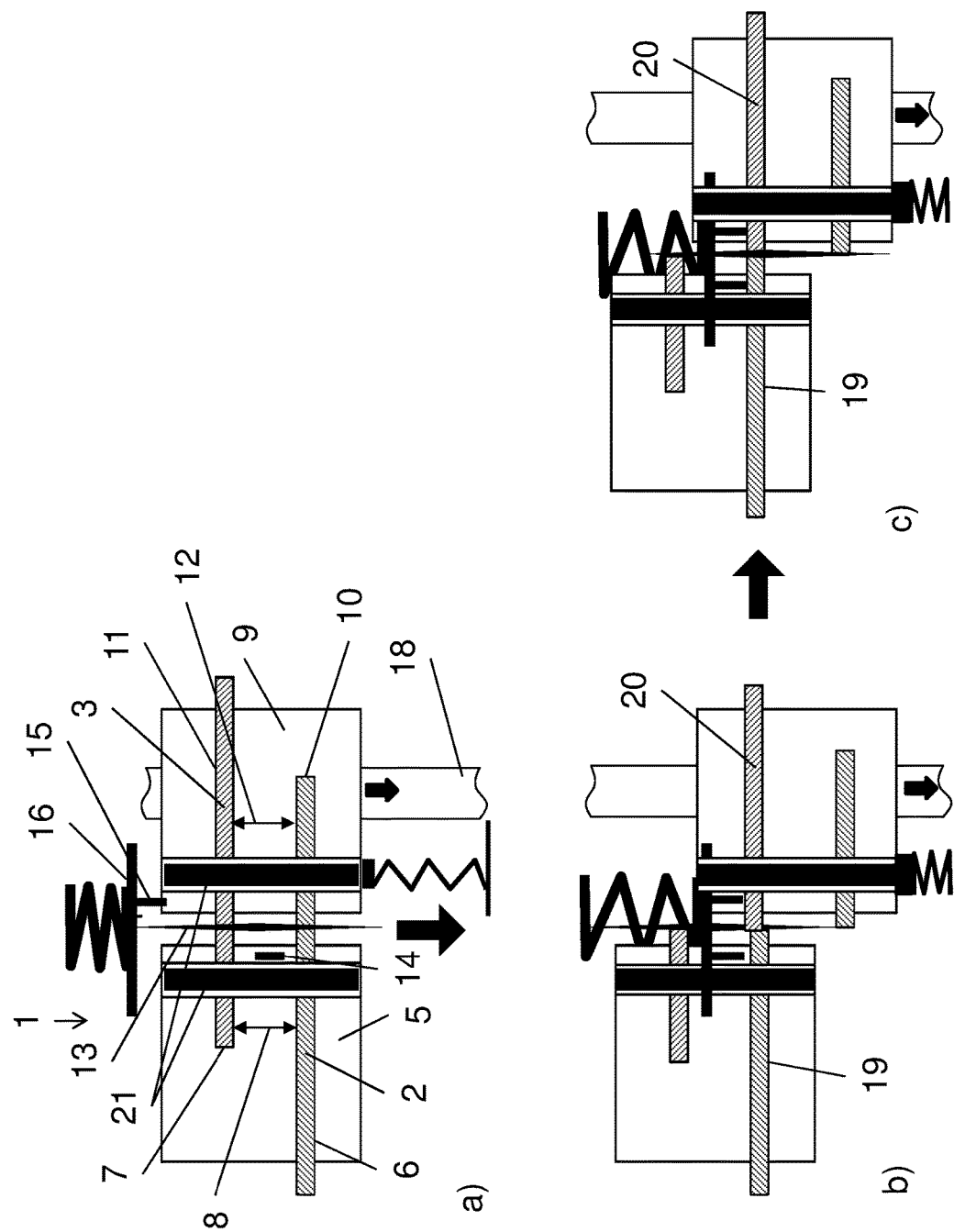
FIG. 4 shows an apparatus of the invention (top view) with the holders a) in the cutting position, b) almost in the welding position and c) in the welding position with the tubing lengths aligned.

In one aspect, as illustrated by FIGS. 1-8, the present invention discloses an apparatus 1;101 for aligning and supporting a first 2;102 and a second 3;103 length of thermoplastic tubing, preparatory to and during cutting and welding of the lengths of tubing. Suitably, both lengths of tubing have the same diameter. The apparatus comprises the following components arranged on a base support 4:

a) a first holder 5;105 arranged to accommodate portions of the first 2;102 and second 3;103 lengths of tubing in a first 6;106 and a second 7;107 elongated holding space respectively, wherein the two holding spaces are essentially parallel to each other and separated from each other by a first distance 8;108. The length axes of the two holding spaces can be arranged at an angle of less than 5 degrees, such as less than 2 degrees or less than 1 degree towards each other.

b) a second holder 9;109 arranged to accommodate (other) portions of the first 2;102 and second 3;103 lengths of tubing in a third 10;110 and a fourth 11;111 elongated holding space respectively, wherein these holding spaces are essentially parallel to each other and to the holding spaces in the first holder (i.e. with the length axes at an angle of less than 5 degrees, such as less than 2 degrees or less than 1 degree towards each other) and separated from each other by a second distance 12;112 substantially the same as the first distance 8;108 (or differing from the first distance by less than 2% or less than 1%), and wherein this second holder is movable, e.g. slidable, in a direction essentially perpendicular to the holding spaces of the first and second holders from a cutting position where the first holding space 6;106 is aligned with the third holding space 10 and said second holding space 7;107 is aligned with said fourth holding space 11;111 to a welding position where said first holding space 6;106 is aligned with said fourth holding space 11;111. This is to say that in the cutting position portions of the first length of tubing 2;102 can be accommodated in the first 6;106 and third 10;110 holding spaces, while portions of the second length of tubing 3;103 can be accommodated in the second 7;107 and fourth 11;111 holding spaces. In the welding position a cut portion 19;119 of the first 2;102 length of tubing can be accommodated in the first holding space 6;106 and aligned with a cut portion 20;120 of the second 3;103 length of tubing accommodated in the fourth holding space 11;111.;

c) Cutting means 13;113 arranged between the first and second holders for cutting the lengths of tubing when the second holder is in the cutting position. The cutting means can be a hot cutting device such as e.g. a heated wafer, a heated wire or a laser beam. It can also be a sharp cold blade, although in this case a sterilant may have to be supplied in order to ensure sterility of the cut ends. The cutting means is suitably arranged to cut both lengths of tubing in an essentially transverse direction, such as at an angle of 85-95 degrees or 88-92 degrees to the length axis of each length of tubing. Throughout this specification, the wording "cutter" can be used interchangeably with "cutting means".

d) Aligning means arranged to abut the outside of a cut length of tubing 19;119 accommodated in the first holding space 6;106 and the outside of a cut length of tubing 20;120 accommodated in the fourth holding space 11;111 and to align these lengths of tubing with each other, typically in the transverse direction, when the second holder is in or is approaching the welding position. As the alignment is done directly by abutment of the outsides of the cut lengths of tubing, proper alignment is ensured irrespective of their diameter. The aligning means may comprise a first 14;114 and a second 15;115 aligning plate, both having substantially the same width 17;117, each movable in a direction essentially perpendicular to (or at an angle of 85-95 degrees, such as 88-92 degrees to) the holding spaces of the first and second holders, and an abutment plate 16;116 attached to said base support, wherein, when the second holder is in the welding position, said first aligning plate is arranged to abut said abutment plate and the outside of the cut length of tubing accommodated in the first holding space 6;106 and said second aligning plate is arranged to abut said abutment plate and the outside of the cut length of tubing accommodated in the fourth holding space 11;111 such that the cut lengths of tubing in the first and second holding spaces are aligned with each other, typically in the transverse direction. Transverse alignment is important, as any misalignment diminishes the contact area in the weld and can easily lead to leakage and/or mechanical failure of the weld joint. The disclosed abutment solution can be produced to a low cost, particularly compared to precision-controlled drives and precision machined parts for placing the holders at exactly determined positions. The aligning by abutment for flexible tubing works particularly well with tubes that have been pinched flat using clamps (see below) in that the side of a flattened tube is considerably more rigid than the non-flattened flexible tube and a higher abutment force can be applied to ensure alignment. The aligning plates may e.g. be slidable on a guideway against a spring load (The spring load will let the plates revert to home position after the operation). The face of the plate that abuts the tube can suitably be flat to ensure that the tube edge is always contacted.

Alternatively the aligning means may comprise a plate driven by a separate drive. This could be a plate which will move to and forth on a rack and pinion arrangement or on a worm gear arrangement or even a linear drive. It could be two plates slidable on each other or any arrangement which permits relative motion between the plates and between the plate and holder.

Figure 5:
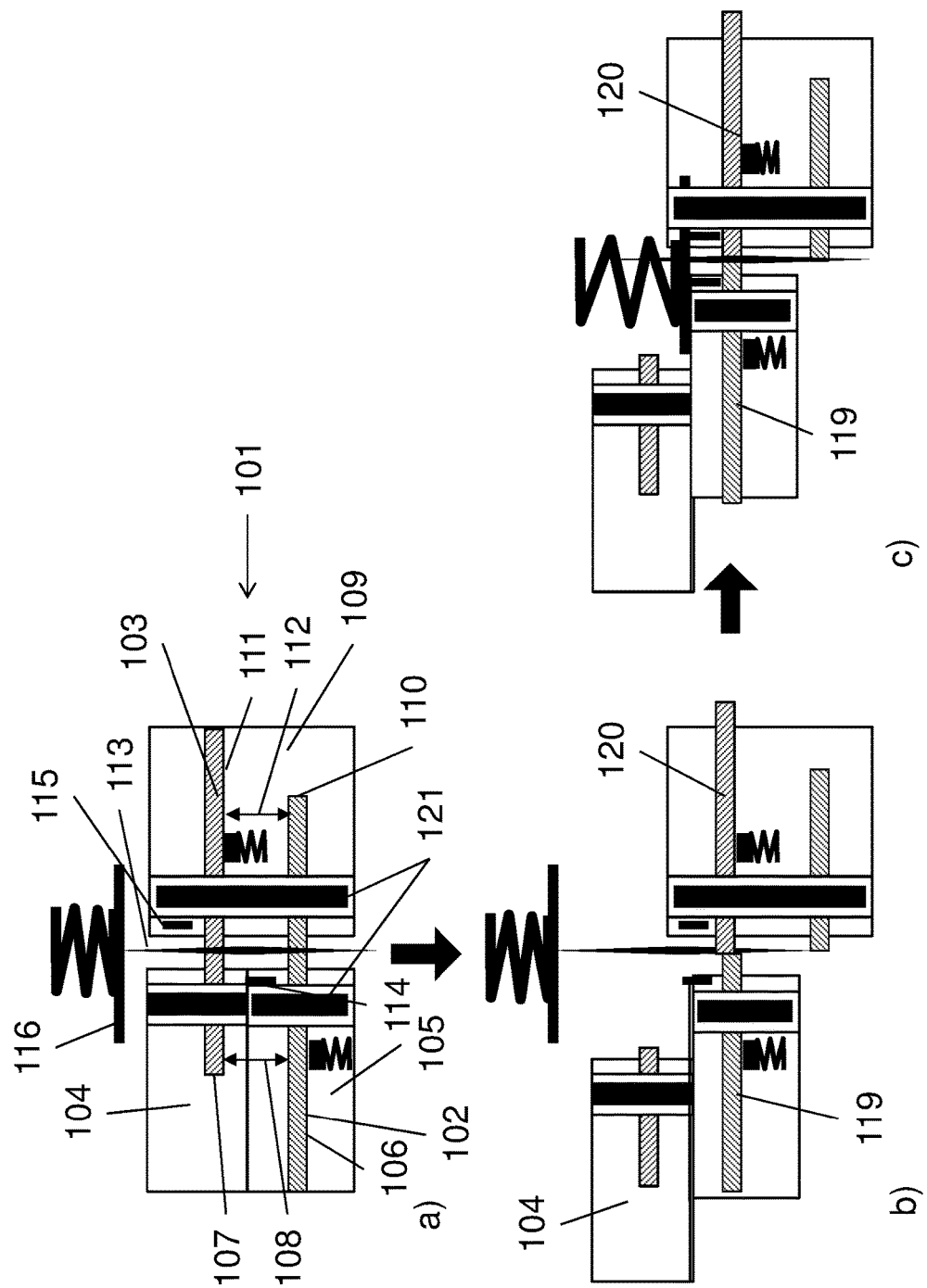
FIG. 5 shows an alternative embodiment of the apparatus of the invention (top view) with the holders a) in the cutting position, b) almost in the welding position and c) in the welding position with the tubing lengths aligned.

One or both of the holders may be dividable, as illustrated in FIG. 5. Here, the first holder 105 is dividable into two parts 105,104 when the second holder approaches the welding position. This arrangement has the advantage that access of the aligning plates 114, 115 and the abutment plate 116 to the cut tubing portions 119, 120 is facilitated. It is however also possible to use non-dividable holders as shown in FIGS. 1-4 and 6, particularly if the holders comprise recesses to accommodate the aligning and abutment plates into suitable positions.

In some embodiments, the apparatus further comprises a heater arranged to heat and weld together the ends of a cut length of tubing accommodated in the first holding space 6;106 and a cut length of tubing accommodated in the fourth holding space 11;111 and wherein said first and second holder are arranged to be urged together to accomplish a welded seal. If a heated wafer is used as cutting means, the same heater wafer can also be the heater, but the heater can also be a separate device, e.g. another wafer, a laser, an infrared beam, a hot air source etc. An advantage of using a single heated wafer for both cutting and welding is that the cut ends can be kept in contact with the hot wafer during the entire operation, thus ensuring aseptic conditions. The urging together of the first and second holders can e.g. be achieved by arranging them to be slidable along one or two guides when in the welding position.

In some embodiments, the first and second alignment plates are arranged to slide against the abutment plate when said first and second holder are urged together. Sliding against the abutment plate is a way to ensure that the alignment is maintained when the holders are urged together.

In certain embodiments, the abutment plate is spring loaded. The spring loading can e.g. be achieved by a helical spring and has the advantage that a suitable force is constantly applied to the aligning plates in order to ensure the alignment.

In some embodiments, the second holder is slidable along a guide 18. This ensures a smooth and precise motion between the cutting and welding positions and facilitates the alignment with the aligning means.

In certain embodiments, the first, second, third and fourth holding spaces are arranged to accommodate tubing lengths having a range of outer diameters, such as a range of 4-25 mm, 4-10 mm, 10-25 mm, 5-20 mm or 7-15 mm. Tubing with different outer diameters in the 4-25 mm range is commonly used in bioprocess settings and to allow a broad scope of use for the apparatus it is advantageous if it can handle either the entire range or significant parts of it. The holding spaces can be constructed as described below or they may e.g. be of large diameter and accommodate sets of smaller diameter cylindrical inserts which can be exchanged depending on the tubing diameter to be used.

Figure 6:
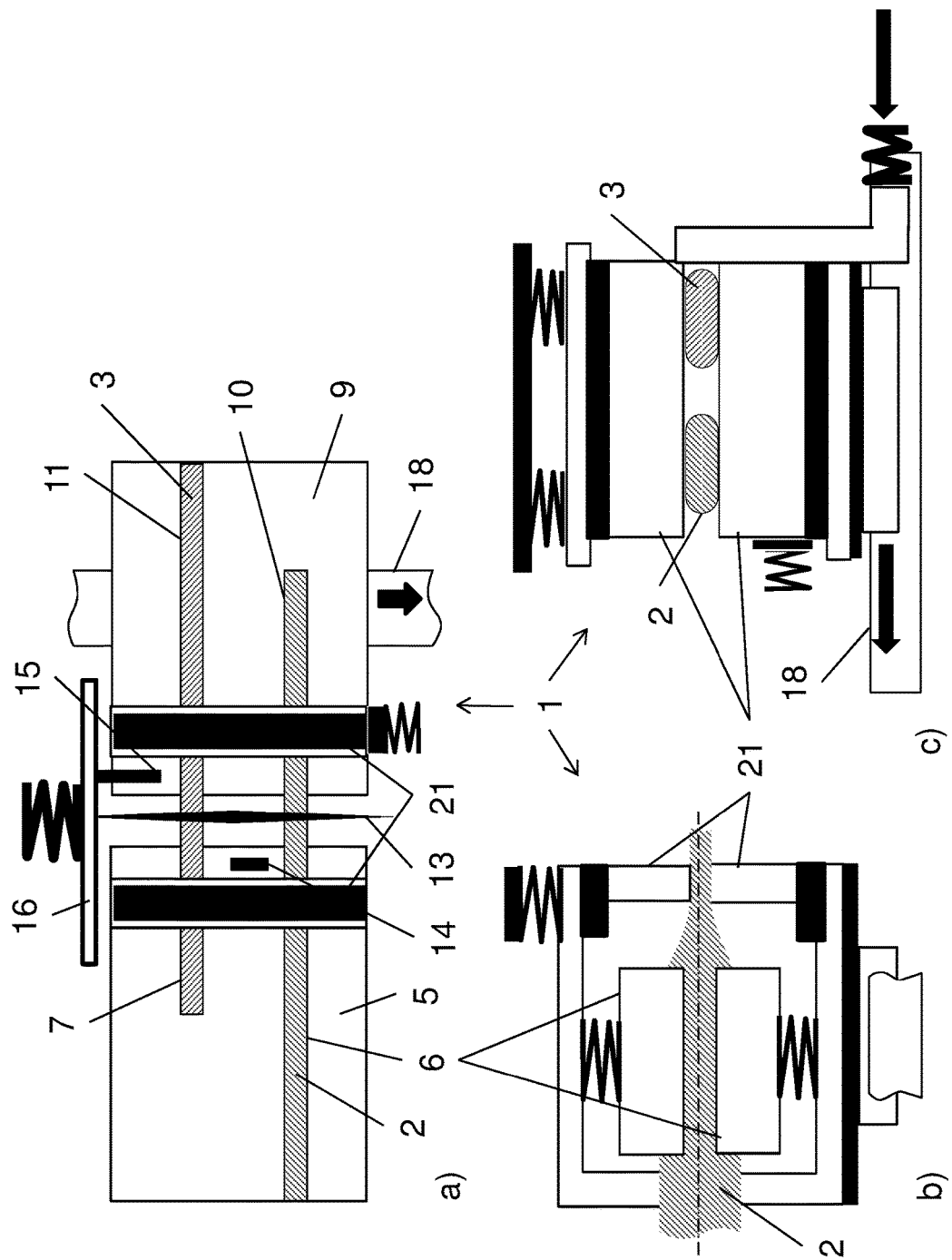
FIG. 6 shows an apparatus of the invention in a) top view, b) side view and c) front view with b) and c) also showing v blocks for accommodating different tube sizes and jaws for clamping the tubes.
Figure 7:
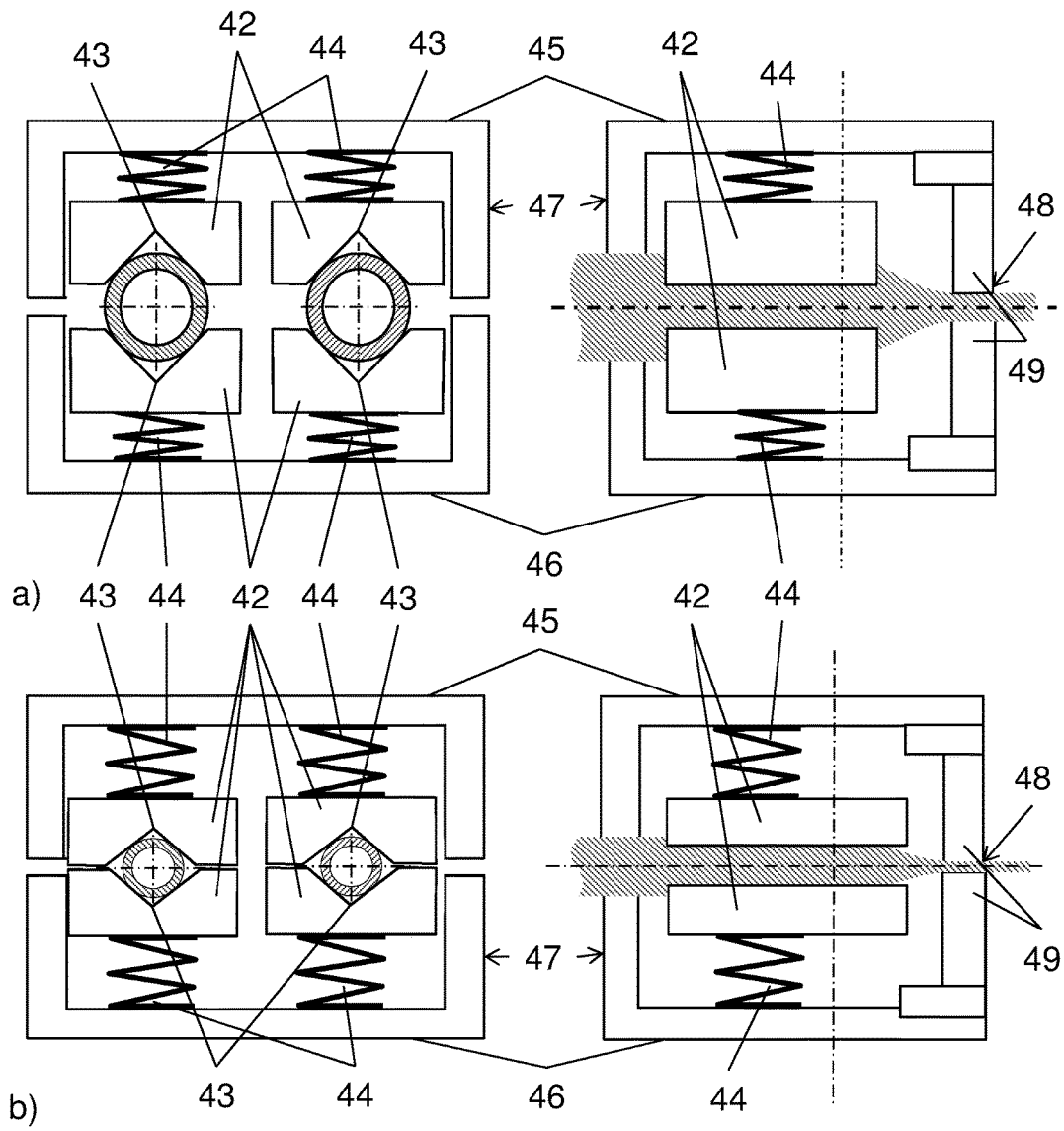
FIG. 7 shows the v blocks for accommodating different tube sizes (front and side view) with a) large diameter tubing and b) small diameter tubing.

In some embodiments, illustrated by FIGS. 6-7, each of said holding spaces comprises two elongated spring loaded opposite v blocks 42 arranged to align the center axes of the tubing lengths along the center axes of the holding spaces. The v blocks can suitably be two elongated blocks, each having a v-shaped groove along the center axis of the holding space, with the v-shaped grooves of each block facing each other. With the spring-loaded v-block arrangement it is possible to accommodate tubing of a wide diameter range and at the same time obtain an axial alignment of the tubing portions to be welded such that a straight transverse weld is obtained. This is important, as misalignment may lead to mechanical failure and/or leakage. The axial alignment is cooperative with the transverse alignment in that both are needed and that even a minimal misalignment in one direction further increases the need for precision alignment in the other direction. When clamping is used (see below), the v-block arrangement further ensures that the clamping force is applied centrally on the tubing. This is important, as non-central clamping can lead to transverse movement of the flattened tube. Although the alignment means are able to obtain alignment even of transversely dislocated tubing ends, the alignment operation is easier if the tubing ends are at the appropriate places. Non-central clamping can also lead to incomplete flattening of the tubes and consequential leakage of liquid.

In certain embodiments, illustrated by FIG. 7, each holding space comprises two v blocks 42 arranged vertically above each other, with the v-shaped grooves 43 facing each other and with the blocks suspended by helical springs 44 from the top 45 and bottom 46 of a frame 47. With this arrangement, the tubing can be accommodated between the v-shaped grooves and the helical springs allow movement of the blocks while applying a suitable force urging the blocks together to hold the tubing length in place and axially aligned without deformation of the tubing. Each block can suitably be suspended by a plurality of helical springs, such as two helical springs. With this solution the lengths of tubing will self-align and no active axial alignment is needed to be performed by the operator.

In certain embodiments each holder comprises a clamp 21;48;51 arranged to flatten a portion of a length of tubing accommodated in the holding spaces. In wet welding, where at least one of the lengths of tubing contains a liquid, the tubes need to be pinched in order to arrest the liquid inside the tube(s) while cutting and welding. The tubes will then be compressed to an essentially flat shape (e.g. such that opposite inside surfaces of the tubing are in direct contact with each other) and cut and welded in this shape. After welding, the clamps are released and the tubes with the weld spring back to cylindrical shape, if necessary assisted by lightly twisting the joint manually. The degree of compression needed depends on the diameter and thickness of the tube, but can typically be about 30% of the combined thickness of the two wall (i.e. 2 times the wall thickness). An upper limit to the compression can typically be up to a level where plastic deformation for the particular material begins. Proper alignment in both the transverse and axial directions is highly desirable in order to get a good flat weld that can spring back to form a good cylindrical weld that does not reduce flow rates through the tubing.

Figure 8:
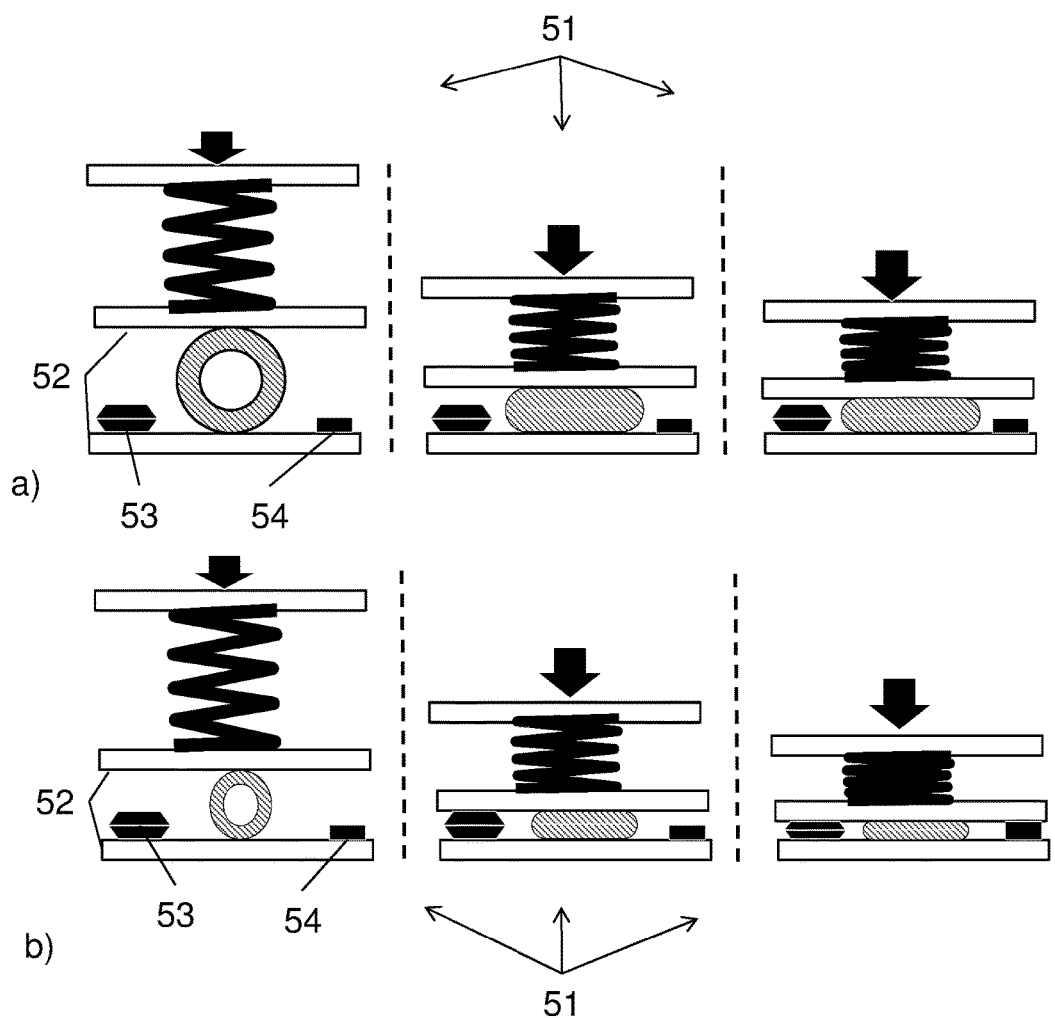
FIG. 8 shows the clamps with different clamping forces applied on a) large diameter tubing and b) small diameter tubing.

In some embodiments, illustrated by FIG. 8, each clamp 51 comprises two jaws 52 and between the jaws at least one compression spring 53 and at least one stopper 54. The at least one compression spring may e.g. be arranged to limit the compression load on tubing of less than 20 mm outer diameter and the at least one stopper may e.g. be arranged to prevent over-compression of tubing with an outer diameter of less than 10 mm. The compression springs can e.g. be disc springs. The compression springs can be arranged to engage both jaws when the jaws are at a distance of up to 20 mm from each other, such as at a distance of up to 8, 10 or 15 mm from each other. The stoppers can e.g. be arranged to engage both jaws at a distance of 4-10 mm from each other, such as 4-7 mm or 5-10 mm from each other. Sufficient compression is needed to prevent any leakage of liquid during cutting and welding, but over-compression can damage the tubing material and also cause undesirable deformation during welding. It may e.g. lead to closed welds that do not spring back upon release of the clamps.

In a second aspect the present invention discloses a method of cutting and welding a first 2;102 and a second 3;103 length of thermoplastic tubing, comprising the steps of:

a) providing an apparatus as disclosed above, with the holders arranged in the cutting position;

b) placing the first length of tubing in the first 6;106 and third 10;110 holding spaces and the second length of tubing in the second 7;107 and fourth 11;111 holding spaces;

c) cutting the first and second lengths of tubing with the cutting means 13;113;

d) sliding the second holder to the welding position;

e) adjusting the positions of the second holder and the first and second aligning plates until both aligning plates abut the abutment plate and the outsides of the cut lengths of tubing;

f) urging the first and second holders together and welding the cut lengths of tubing to form a seam.

In some embodiments the method comprises, between steps b) and c), a step b') of clamping both the first and second length of tubing to an essentially flat shape (e.g. such that opposite inside surfaces of the tubing are in direct contact with each other). As discussed above, this facilitates welding when liquid is present in at least one of the lengths of tubing. When a clamping step is used, the tubing used can suitably be flexible, such as tubing manufactured from e.g. thermoplastic elastomers or plasticized PVC. The method can further, after step f) comprise a step f') of releasing the clamping.

In a third aspect the present invention discloses an apparatus 1;101 for aligning and supporting a first 2;102 and a second 3;103 length of thermoplastic tubing, preparatory to and during cutting and welding of said lengths of tubing, said apparatus comprising the following components arranged on a base support 4:

a) a first holder 5;105 arranged to accommodate portions of said first and second lengths of tubing in a first 6;106 and a second 7;107 elongated holding space respectively, wherein said holding spaces are essentially parallel to each other and separated from each other by a first distance 8;108;

b) a second holder 9;109 arranged to accommodate portions of said first and second lengths of tubing in a third 10;110 and a fourth 11;111 elongated holding space respectively, wherein said holding spaces are essentially parallel to each other and to the holding spaces in the first holder and separated from each other by a second distance 12;112 substantially the same as the first distance 8;108, and wherein said second holder is slidable in a direction essentially perpendicular to the holding spaces of the first and second holders from a cutting position where said first holding space 6;106 is aligned with said third holding space 10;110 and said second holding space 7;107 is aligned with said fourth holding space 11;111 to a welding position where said first holding space 6;106 is aligned with said fourth holding space 11;111;

c) cutting means 13;113 arranged between said first and second holders for cutting said lengths of tubing when the second holder is in the cutting position, wherein each of said first, second, third and fourth holding spaces comprises two elongated spring loaded opposite v blocks 42, as defined above, arranged to align the center axes of the tubing lengths along the center axes of the holding spaces.

In certain embodiments each holding space comprises two v blocks 42 arranged vertically above each other, with the v-shaped grooves 43 facing each other and with the blocks suspended by helical springs 44 from the top 45 and bottom 46 of a frame 47.

In a fourth aspect the present invention discloses an apparatus 1;101 for aligning and supporting a first 2;102 and a second 3;103 length of thermoplastic tubing, preparatory to and during cutting and welding of said lengths of tubing, said apparatus comprising the following components arranged on a base support 4:

a) a first holder 5;105 arranged to accommodate portions of said first and second lengths of tubing in a first 6;106 and a second 7;107 elongated holding space respectively, wherein said holding spaces are essentially parallel to each other and separated from each other by a first distance 8;108;

b) a second holder 9;109 arranged to accommodate portions of said first and second lengths of tubing in a third 10;110 and a fourth 11;111 elongated holding space respectively, wherein said holding spaces are essentially parallel to each other and to the holding spaces in the first holder and separated from each other by a second distance 12;112 substantially the same as the first distance 8;108, and wherein said second holder is slidable in a direction essentially perpendicular to the holding spaces of the first and second holders from a cutting position where said first holding space 6;106 is aligned with said third holding space 10;110 and said second holding space 7;107 is aligned with said fourth holding space 11;111 to a welding position where said first holding space 6;106 is aligned with said fourth holding space 11;111;

c) cutting means 13;113 arranged between said first and second holders for cutting said lengths of tubing when the second holder is in the cutting position, d) in each holder, a clamp 51 arranged to flatten a portion of a length of tubing accommodated in the holding spaces, wherein each clamp 51 comprises two jaws 52 and between the jaws at least one compression spring 53 and at least one stopper 54.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An apparatus for aligning and supporting a first and a second length of thermoplastic tubing, preparatory to and during cutting and welding of said lengths of tubing, said apparatus comprising the following components arranged on a base support:
    a) a first holder having first and second elongated holding spaces arranged to accommodate portions of said first and second lengths of tubing in the first and second elongated holding spaces, respectively, wherein said first and second holding spaces are essentially parallel to each other and separated from each other by a first distance;
    b) a second holder having third and fourth elongated holding spaces arranged to accommodate portions of said first and second lengths of tubing in the third and fourth elongated holding spaces, respectively, wherein said third and fourth holding spaces are essentially parallel to each other and to the holding spaces in the first holder and separated from each other by a second distance substantially the same as the first distance, and wherein said second holder is movable in a direction essentially perpendicular to the holding spaces of the first and second holders from a cutting position where said first holding space is aligned with said third holding space and said second holding space is aligned with said fourth holding space to a welding position where said first holding space is aligned with said fourth holding space;
    c) cutting means arranged between said first and second holders for cutting said lengths of tubing when the second holder is in the cutting position, and;
    d) aligning means which are movable relative to the first and second holders and are arranged to abut the outside of a cut length of tubing accommodated in the first holding space and the outside of a cut length of tubing accommodated in the fourth holding space and to align these lengths of tubing with each other.

2. The apparatus of claim 1, wherein the aligning means comprises first and second aligning plates, both having substantially the same width, each movable in a direction essentially perpendicular to the holding spaces of the first and second holders, and an abutment plate attached to said base support, wherein, when the second holder is in the welding position, said first aligning plate is arranged to abut said abutment plate and the outside of a cut length of tubing accommodated in the first holding space and said second aligning plate is arranged to abut said abutment plate and the outside of a cut length of tubing accommodated in the fourth holding space such that the cut lengths of tubing in the first and fourth holding spaces are aligned with each other.

3. The apparatus of claim 2, wherein said first and second aligning plates are arranged to slide against the abutment plate when said first and second holders are urged together.

4. The apparatus of claim 2, wherein said abutment plate is spring loaded.

5. The apparatus of claim 1, further comprising a heater arranged to heat and weld together the ends of a cut length of tubing accommodated in the first holding space and a cut length of tubing accommodated in the fourth holding space and wherein said first and second holders are arranged to be urged together to accomplish a welded seal.

6. The apparatus of claim 1, wherein said second holder is slidable along a guide.

7. The apparatus of claim 1 wherein said first, second, third and fourth holding spaces are arranged to accommodate tubing lengths having a range of outer diameters.

8. The apparatus of claim 1, wherein each of said holding spaces comprises two elongated spring loaded opposite v blocks arranged to align the center axes of the respective tubing lengths along the center axes of the respective holding spaces, each v block comprising a v-shaped channel positioned along a center axis of its respective holding space.

9. The apparatus of claim 8, wherein the two v blocks of each respective holding space are arranged vertically one above the other, with their v-shaped channels facing each other and with the v blocks suspended by helical springs from the top and bottom of a frame.

10. The apparatus of claim 1, wherein each holder comprises a clamp arranged to flatten a portion of the lengths of tubing accommodated in the respective holding spaces.

11. The apparatus of claim 10, wherein each clamp comprises two jaws and between the jaws at least one compression spring and at least one stopper.

12. The apparatus of claim 11, wherein the at least one compression spring is arranged to limit the compression load on tubing of less than 20 mm outer diameter and the at least one stopper is arranged to prevent over-compression of tubing with an outer diameter of less than 10 mm.

13. The apparatus of claim 12, wherein each compression spring is a disc spring.

14. The apparatus of claim 12, wherein each compression spring is arranged to engage both respective jaws when the respective jaws are at a distance of up to 20 mm from each other.

15. The apparatus of claim 12, wherein each stopper is arranged to engage both respective jaws at a distance of 4-10 mm from each other.

16. A method of cutting and welding a first and a second length of thermoplastic tubing, comprising the steps of:
a) providing the apparatus of claim 1, with the holders arranged in the cutting position;
b) placing the first length of tubing in the first and third holding spaces and the second length of tubing in the second and fourth holding spaces;
c) cutting the first and second lengths of tubing with the cutting means;
d) sliding the second holder to the welding position;
e) adjusting the positions of the second holder and the aligning means until the aligning means abut the abutment plate and the outsides of the respective cut lengths of tubing;
f) urging the first and second holders together and welding the cut lengths of tubing to form a seam.

17. The method of claim 16, further comprising, between steps b) and c), a step b') of clamping both the first and second lengths of tubing to an essentially flat shape.

18. An apparatus for aligning and supporting a first and a second length of thermoplastic tubing, preparatory to and during cutting and welding of said lengths of tubing, said apparatus comprising the following components arranged on a base support:
a) a first holder having first and second elongated holding spaces arranged to accommodate portions of said first and second lengths of tubing in the first and second elongated holding spaces, respectively, wherein said first and second holding spaces are essentially parallel to each other and separated from each other by a first distance;
b) a second holder having third and fourth elongated holding spaces arranged to accommodate portions of said first and second lengths of tubing in the third and fourth elongated holding spaces, respectively, wherein said third and fourth holding spaces are essentially parallel to each other and to the holding spaces in the first holder and separated from each other by a second distance substantially the same as the first distance, and wherein said second holder is slidable in a direction essentially perpendicular to the holding spaces of the first and second holders from a cutting position where said first holding space is aligned with said third holding space and said second holding space is aligned with said fourth holding space to a welding position where said first holding space is aligned with said fourth holding space, and;
c) cutting means arranged between said first and second holders for cutting said lengths of tubing when the second holder is in the cutting position,
wherein each of said first, second, third and fourth holding spaces comprises two elongated spring loaded opposite v blocks arranged to align the center axes of the respective tubing lengths along the center axes of the respective holding spaces, each v block comprising a v-shaped channel positioned along a center axis of its respective holding space, and
wherein each holder comprises a clamp arranged to flatten a portion of a length of tubing accommodated in the respective holding spaces, and wherein each clamp comprises two jaws and between the jaws at least one compression spring and at least one stopper.

19. The apparatus according to claim 18, wherein the two v blocks of each holding space are arranged vertically one above the other, with their v-shaped channels facing each other and with the v blocks suspended by helical springs from the top and bottom of a frame.

20. An apparatus for aligning and supporting a first and a second length of thermoplastic tubing, preparatory to and during cutting and welding of said lengths of tubing, said apparatus comprising the following components arranged on a base support:
- a) a first holder having first and second elongated holding spaces arranged to accommodate portions of said first and second lengths of tubing in the first and second elongated holding spaces, respectively, wherein said first and second holding spaces are essentially parallel to each other and separated from each other by a first distance;
- b) a second holder having third and fourth elongated holding spaces arranged to accommodate portions of said first and second lengths of tubing in the third and fourth elongated holding spaces, respectively, wherein said third and fourth holding spaces are essentially parallel to each other and to the holding spaces in the first holder and separated from each other by a second distance substantially the same as the first distance, and wherein said second holder is slidable in a direction essentially perpendicular to the holding spaces of the first and second holders from a cutting position where said first holding space is aligned with said third holding space and said second holding space is aligned with said fourth holding space to a welding position where said first holding space is aligned with said fourth holding space;
- c) cutting means arranged between said first and second holders for cutting said lengths of tubing when the second holder is in the cutting position, and;
- d) in each holder, a clamp arranged to flatten a portion of a length of tubing accommodated in the respective holding spaces, wherein each clamp comprises two jaws and between the jaws at least one compression spring and at least one stopper.

* * * * *